United States Patent
Woller et al.

[11] Patent Number: 5,902,600
[45] Date of Patent: May 11, 1999

[54] HYDROGEL POLYMER WOUND DRESSING

[75] Inventors: William H. Woller; David P. Jones, both of San Antonio, Tex.

[73] Assignee: Healthpoint, Ltd., San Antonio, Tex.

[21] Appl. No.: 07/994,536

[22] Filed: Dec. 21, 1992

[51] Int. Cl.⁶ ..................................................... A61L 16/00
[52] U.S. Cl. ..................... 424/445; 424/78.06; 514/944
[58] Field of Search ................... 424/445, 60, 78.06; 514/944

[56] References Cited

U.S. PATENT DOCUMENTS

| | | | |
|---|---|---|---|
| 3,542,562 | 11/1970 | Cooke et al. | 99/94 |
| 4,226,232 | 10/1980 | Spence | 128/156 |
| 4,594,240 | 6/1986 | Kawata et al. | 424/28 |
| 4,746,514 | 5/1988 | Warne | 414/445 |
| 4,781,923 | 11/1988 | Pellico | 424/595 |
| 4,837,019 | 6/1989 | Georgalas | 424/60 |
| 4,885,161 | 12/1989 | Cornell | 424/78 |
| 4,889,530 | 12/1989 | Smith et al. | 603/304 |
| 5,063,057 | 11/1991 | Spellman et al. | 424/401 |
| 5,076,265 | 12/1991 | Wokalek | 128/156 |
| 5,112,618 | 5/1992 | Cartmell et al. | 424/443 |
| 5,116,621 | 5/1992 | Oji et al. | 424/445 |

*Primary Examiner*—D. Gabrielle Brouillette
*Attorney, Agent, or Firm*—Zarley, McKee, Thomte, Voorhees & Sease

[57] ABSTRACT

A hydrogel wound dressing is provided which is clear, non greasy, water soluble and odor free. The wound dressing additionally does not exhibit any thickening properties and is of a viscosity such that it will adhere to the wound bed to facilitate natural healing yet will also be easily removable with water and will not stick to the wound or gauze, allowing for removal of bandages without tearing of delicate regenerated skin. The wound dressing also contains humectant properties such that the wound is kept hydrated to prevent any scabbing or drying out so that the wound is allowed to heal from the inside out.

4 Claims, No Drawings

HYDROGEL POLYMER WOUND DRESSING

BACKGROUND OF THE INVENTION

Treatment of superficial wounds such as Stage I-IV pressure ulcers, stasis ulcers, first and second degree burns, cuts, abrasions and other minor irritations of the skin present several inconveniences for both health care personnel and patients. Such wounds are highly susceptible to bacterial infections and thus maintenance of cleanliness of the healing surface is desirable. Additionally, foreign particles may become incorporated into the wound surface as it heals over. Response to this problem has lead to wound dressings covering the injured area as it heals.

Conventional wound dressings usually involve a fabric or felt of absorptive material such as gauze in direct contact with the wound. Such conventional dressings are normally covered in order to avoid or reduce bacterial contamination but the dressing itself is not efficient in this respect. They do have the general advantage of absorbing exudate from the wound, but on the other hand, tend to stick to the wound surface thus inhibiting healing. Furthermore, removal of the dressing is commonly painful and disruptive where such adherence has occurred. Thus, benefits of covering the wound are accompanied by a host of other problems as the wound begins to scab over. Additionally scabbing often entraps foreign material hindering healing and will limit movement of the patient when the injury occurs in an area of the skin which is stretched in response to joint movement, such as the knee. Ideal healing occurs from the inside out.

A recent advancement has been the use and development of hydrogel polymer wound dressings, including polysaccharides, proteins and polypeptides. These gels prevent drying and eventually scabbing of the sore due to a markably strong bonding of water with the polymer molecule. A particular feature of these hydrogel dressings is that they resist entry of bacteria and thus maintain cleanliness of the healing surface, whereas fabric coverings being porous tend to permit bacterial invasion. The gel form of the wound dressing is beneficial in that it is easily deliverable from soft tubes. However even with hydrogels there is always the conflict between desirable properties for would dressing and packaging, i.e. between a gel which is easy to package but too soft and flowable which will simply run out of the wound and not adequately adhere, and on the other hand the more viscous products which are difficult to package and dispense from containers, and too sticky causing tissue damage or which hinder wound cleansing.

Current wound dressings in use include petroleum jellies. These dressings however can form a dry film leading to the problems earlier discussed as to sticking to the gauze bandage and tearing of the delicate regenerated skin upon removal. Another conventional dressing includes paraffins and petroleums. These however are not water soluble and present difficulties in removal during wound cleansing.

The advancements in the area of water hydrated compounds for use as wound dressings has also presented difficulties. One such hydrophilic material which would seem promising is glycerin; however, use of glycerin alone is not workable in that it is not viscous enough. When placed on a wound, glycerin, particularly after water absorption, will simply fall out of the wound. Other such gels as disclosed in Smith et al U.S. Pat. No. 4,889,530 tend to be viscous enough to adhere to the wound but go too far in the other direction in that they posses thickening properties when applied to the wound such that upon removal during cleansing they often tear delicate regenerated tissue.

A common problem even for hydrogels, is that the product must be able to adhere to both moist and dry skin and yet be easily removable during wound washing. If one emphasizes water solubility in formulation to allow easy washing removal, wound adherence is compromised along with the desirable protectant function from contamination. Moreover increased water solubility often means "drying out" which creates further problems in wound healing.

It is an object of the present invention to provide a hydrogel polymer based wound dressing of a viscosity such that it will adhere to the wound to provide moistness and yet is easily water soluble and non thickening such that it may be removed without tearing delicate regenerated tissue.

Yet another object of the invention is to provide a clear viscous hydrogel which will protect the wound bed from foreign contaminants and bacteria to enhance the natural healing process.

Yet another object of the invention is to provide a wound dressing which may be easily dispensed in gel form from a soft tube container.

A still further object of the invention is to provide a wound dressing which will promote healing of the wound from the inside out by keeping the wound moist to prevent drying and scab formation as well as effective protection from infection.

Further objects of the invention will come apparent in the description of the invention which follows.

SUMMARY OF THE INVENTION

This invention relates to a wound dressing in the form of a combination of a certain hydrogel polymer and a humectant, preferably glycerin. The composition will not dry out due to very strong affinity for water and the polymer is viscous enough to remain in the wound bed. The ingredients coact to prevent significant thickening or drying. This allows for easy removal without damage to underlying skin. The composition comprises a nontoxic, compatible polyhydric alcohol humectant in combination with glycerin polyacrylate. The composition includes from about 10 percent to 50 percent by weight of the polyhydric alcohol, preferably glycerin, and 40 percent to 80 percent blend of glycerin polyacrylate. The two compounds are easily miscible with each other, and when mixed in proper amounts to form a gel which is of the desired viscosity for keeping the wound hydrated, and protected from external irritants.

DETAILED DESCRIPTION OF THE INVENTION

The polymer and glycerin mixture used in the present invention exhibit remarkably strong holding capacity of water with the molecule and yet when flooded with water during washing can be easily removed. Thus the composition prevents water evaporation from the wound and inhibits the drying associated with scabbing and sticking to a gauze cover. The first compound of the wound dressing is a polyhydric alcohol of the general formula:

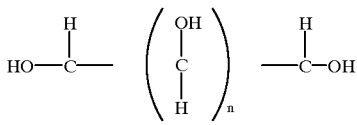

wherein n represents the number of repeating CHOH units. This substance is preferably glycerin, a common humectant having a high affinity for water. It also has an affinity for the glycerol moiety of the hydrogel allowing easy blending formulation. The hydrogel is a polymer blend of glycerin polyacrylate.

Glycerin polyacrylate is hydrated clatharate acrylic acid polymer in glycerin. Acrylic acid polymer may be depicted as:

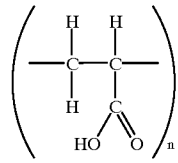

wherein n represents the number of repeating units.

One commercial source for obtaining the glycerin polyacrylate polymer is a chemical available under the tradename Hispagel® distributed by Center Chem, Inc. of Stamford, Connecticut. The glycerin polyacrylate has excellent water solubility, moisture retention and lubrication properties. Additionally this polymer also has the non drying property due to strong bonding of water with the polymer molecule. The glycerin polyacrylate will work on skin to form a film protecting the wound from outside particles and in combination with glycerin maintain a high hydration level.

Glycerin polyacrylate also, however, has rheological and thickening properties allowing it to act like a jelly. This tends to be a problem with use of glycerin polyacrylate polymer alone as a wound dressing in that it tends to become so thick and sticky that upon removal it will tear the delicate regenerated skin.

Applicants have found that when glycerin polyacrylate is blended with glycerin in specific proportions a wound dressing results which combines all of the favorable properties of the two compounds separately, namely the water hydration capabilities, the jelly forms moist skin protection, a clear product to make the wound visible, and a resulting viscosity such that the product will adhere to the wound to form a protective cover while also being easily removable and water soluble for washing such that the delicate tissue surrounding the wound will not be damaged.

According to Applicant's invention, acceptable ranges for combination of the two polymers include a range of from about 10% to 50% by weight of glycerin combined with a range of from about 40% to 80% by weight of the blend of glycerin polyacrylate. When combined at these ratios the product exhibits the desired viscosity. Preferred ranges of the components include glycerin at 25% to 40% by weight and of the blend of glycerin polyacrylate at 40% to 60% by weight. Optionally in other embodiments of the invention certain preservatives may be added to the composition to reduce contamination and to preserve the polymer products. Such preservatives are well known and include methylparaben, propylparaben, imidurea, diazolidinyl urea and quaterium 15. These preservatives may be added and generally will not account for more than 1 percent of the wound dressing composition.

EXAMPLE

A wound dressing composition according to the invention was prepared comprising the following percentages by weight:

| Component | Percent By Weight |
|---|---|
| Glycerin | 35.0 |
| Methylparaben | 0.173 |
| Propylparaben | 0.023 |
| Glycerin Polyacrylate | 55.0 |
| Purified Water | 9.658 |
| Imidurea | 0.150 |

Upon blending the resultant composition was distributed to nurses for use in treating various minor irritations such as cuts, abrasions, pressure and stasis ulcers, and first and second degree burns. The product was found to be easily dispensable and applicable to patients. The compound was clear, non oily and free of odor.

On application to wounds the product was of a viscosity such that it adhered to the wound bed maintaining hydration of the wounds as they healed properly without undue scabbing or sticking to gauze bandages. The product was easily removed in cleansing. Wounds so treated were able to heal from the inside out and were free of external contaminants. Upon cleansing of the wound and removal of bandages, the dressing did not stick to the bandages and was easily removed with water such that healing skin areas remained intact and did not suffer tearing. Areas treated remained soft and pliable.

As can be seen from the foregoing the invention accomplishes at least all of its objectives.

What is claimed is:

1. A wound dressing composition consisting essentially of:
   from about 40 percent to 80 percent by weight of blended glycerin polyacrylate clatharate;
   from about 10 percent to 50 percent by weight of glycerin as a compatible, non toxic polyhydric alcohol, and; a preservative component comprising from about 0.05 to 0.30 percent by weight of methylparaben; from about 0.01 to 0.10 percent by weight of propylparaben; and from about 0.05 to 0.50 percent by weight of imidurea.

2. The composition of claim 1 wherein the percentage by weight of blended glycerin polyacrylate clatharate is 45 to 60, and the percentage by weight of glycerin is 25 to 40.

3. The composition of claim 1 wherein the percentage by weight of blended glycerin polyacrylate is 55 and the percentage by weight of glycerin is 35.

4. A method of treating superficial wounds and other minor irritations of the skin, said method consisting essential of:
   topically applying the wound dressing composition of claim 1 to a superficial wound bed such that said gel formed a layer on top of the wound bed; and allowing the natural healing process to occur.

* * * * *